(12) United States Patent
Neyts et al.

(10) Patent No.: US 8,343,323 B2
(45) Date of Patent: Jan. 1, 2013

(54) DETERMINATION OF PARTICLE PROPERTIES

(75) Inventors: Kristiaan Neyts, Ghent (BE); Filip Strubbe, Ghent (BE)

(73) Assignee: Universiteit Gent, Gent (BE)

( * ) Notice: Subject to any disclaimer, the term of this patent is extended or adjusted under 35 U.S.C. 154(b) by 203 days.

(21) Appl. No.: 12/988,179

(22) PCT Filed: Apr. 16, 2009

(86) PCT No.: PCT/EP2009/054524
§ 371 (c)(1), (2), (4) Date: Oct. 15, 2010

(87) PCT Pub. No.: WO2009/127688
PCT Pub. Date: Oct. 22, 2009

(65) Prior Publication Data
US 2011/0036719 A1 Feb. 17, 2011

(30) Foreign Application Priority Data
Apr. 16, 2008 (GB) .................................. 0806926.2

(51) Int. Cl.
*G01N 27/447* (2006.01)
*G01N 27/453* (2006.01)
(52) U.S. Cl. ...................................... 204/450; 204/600
(58) Field of Classification Search .......... 204/600–605, 204/450–455
See application file for complete search history.

(56) References Cited

U.S. PATENT DOCUMENTS
3,815,022 A * 6/1974 Golibersuch ................ 324/71.1
4,210,504 A * 7/1980 Friedel et al. ................ 204/549
6,281,972 B1 8/2001 Ebara et al.

OTHER PUBLICATIONS

International Search Report in PCT/EP2009/054524, Dec. 4, 2009.
Knutson, E. O. et al: "Aerosol Classification by Electric Mobility: Apparatus, Theory, and Applications", Journal of Aerosol Science, Elmsford, NY, US, vol. 6, No. 6, Jan. 1, 1975, pp. 443-451, XP008032193.
Hoppel, W. A.: "Determination of the Aerosol Size Distribution from the Mobility Distribution of the Charged Fraction of Aerosols", Journal of Aerosol Science UK, vol. 9, No. 1, Feb. 1978, pp. 41-54, XP002556608.
Scheibel, H. G. et al: "Application of New Charge Distribution Data in the Particle Size Analysis of Ultrafine Aerosol Particles (30 nm > d > 1 nm) with the differential mobility method (DMM)", Journal of Aerosol Science Jun. 1984 US, vol. 15, No. 3, Sep. 14, 1983, pp. 372-375, XP002556609.

* cited by examiner

*Primary Examiner* — Alex Noguerola
(74) *Attorney, Agent, or Firm* — Bacon & Thomas, PLLC

(57) ABSTRACT

The present invention relates to a method and system for determining particle properties. Such properties may for example be charge, size, drift, etc. The method comprises determining (110) an electric mobility distribution based on detection of individual particles. The latter may be performed for a single particle over time, for a plurality of particles at the same time or in a combination thereof. The method also comprises deriving a particle property based on a periodicity in the electric mobility distribution.

17 Claims, 9 Drawing Sheets

| | $\hat{\mu}_v \pm \sigma_{\hat{\mu}_v}$ $(10^{-12}\,m^2/Vs)$ | $\hat{a}$ $(10^{-6}\,m)$ | $\hat{\sigma}$ $(10^{-12}\,m^2/Vs)$ | $\sigma_\mu$ $(10^{-12}\,m^2/Vs)$ | $\sqrt{\frac{1}{N}\sum_i \hat{z}_i^2}$ |
|---|---|---|---|---|---|
| 1 | 6.18 ± 0.05 | 0.996 ± 0.008 | 1.30 | 1.32 | 2.76 |
| 2 | 5.95 ± 0.03 | 1.035 ± 0.006 | 1.31 | 1.31 | 4.48 |
| 3 | 6.10 ± 0.01 | 1.009 ± 0.002 | 1.16 | 1.25 | 8.43 |
| 4 | 6.10 ± 0.03 | 1.010 ± 0.006 | 1.32 | 1.35 | 4.97 |
| 5 | 6.06 ± 0.06 | 1.017 ± 0.011 | 1.25 | 1.21 | 2.11 |
| 6 | 5.97 ± 0.02 | 1.032 ± 0.003 | 1.24 | 1.17 | 9.08 |
| 7 | 5.65 ± 0.06 | 1.089 ± 0.012 | 1.27 | 1.30 | 1.41 |
| 8 | 5.86 ± 0.08 | 1.051 ± 0.014 | 1.34 | 1.29 | 2.26 |
| 9 | 6.21 ± 0.03 | 9.923 ± 0.005 | 1.39 | 1.43 | 6.16 |
| 10 | 6.14 ± 0.05 | 1.003 ± 0.008 | 1.24 | 1.32 | 2.88 |

FIG. 11

DETERMINATION OF PARTICLE PROPERTIES

TECHNICAL FIELD OF THE INVENTION

The present invention relates to characterization of particles and its application. More particularly, the present invention relates to methods and systems for determining particle properties based on electric mobility measurements.

BACKGROUND OF THE INVENTION

The elementary charge e is a fundamental physical constant with a measured value of approximately $1.602176487(40) \times 10^{-19}$ C. It is the smallest measurable value of the electric charge in stable matter, despite many recent attempts to measure fractional charges such as ⅓ e and ⅔ e. Almost 100 years ago, Robert Millikan carried out the first measurement of the value of e by observing the motion of charged oil drops in air under the influence of an electric field. The present invention relates to the measurement of the elementary charge on solid particles in a liquid. Measuring the elementary charge in a liquid is more difficult than in air because of the higher viscosity, which reduces the motion of weakly charged particles in an electric field to a value which may be below the sensitivity of most measurement systems.

The rationale for accurate measurement of small charges is the need for characterization of colloids, for determining the charge and size distribution of colloids, for studying ionic reactions at the surface of particles and for the detection of low concentrations of molecules, where in the ideal case the binding of a single molecule can be registered.

A number of exemplary methods for determining particle characteristics such as for example charge or size is already available on the market. For example, U.S. Pat. No. 6,281,972 describes a method for measuring the size distribution of particles in a gas. The method is based on selecting or classifying the mobility of a plurality of particles and measuring the size of a number of particles. For the different size measurements, the mobility is kept fixed. There still is a need for accurate and/or sensitive measurement techniques for detecting properties of particles, such as for example size or charge.

SUMMARY OF THE INVENTION

It is an object of embodiments of the present invention to provide good apparatus or methods for determining electrical properties and/or size of particles, such as for example colloidal particles or macromolecules.

It is an advantage of embodiments according to the present invention that methods and systems are provided allowing accurate measurement of properties of particles, e.g. individual colloidal particles or macromolecules. The properties may be for example charge, mobility or size. The properties can be determined as function of time. According to at least some embodiments of the present invention, accuracy is reached with error below 1%. The above objective is accomplished by a method and device according to the present invention.

The present invention relates to a method for determining particle properties, the method comprising determining an electric mobility distribution based on detection of individual particles, and deriving a particle property based on a periodicity in the electric mobility distribution. It is an advantage of embodiments according to the present invention that particle properties can be determined with high accuracy. It is an advantage of embodiments according to the present invention that information regarding charge as well as size can be derived.

Determining an electric mobility distribution may comprise determining a plurality of values for the electric mobility of an individual particle and determining an electric mobility distribution based on said plurality of values for the electric mobility. It is an advantage of embodiments according to the present invention that particle properties of individual particles as well as particle properties of particles in a group of particles can be determined.

Determining a plurality of values for the electric mobility of an individual particle may comprise determining a plurality of values for one individual particle over time. It is an advantage of embodiments according to the present invention that methods and systems are provided that allow determining properties of an individual particle.

Determining a plurality of values for the electric mobility of an individual particle may comprise determining for a plurality of particles a value of an electric mobility for each particle individually. It is an advantage of embodiments according to the present invention that an efficient system may be obtained.

Determining a plurality of values for the electric mobility of an individual particle may comprise performing an electrophoretic measurement on at least one individual particle. It is an advantage of embodiments according to the present invention that the basic measurements to be performed are well known in the art, whereby the advantage is obtained by different processing of the obtained results. The latter supports the flexibility for performing these measurements in existing systems.

Determining a plurality of values of the electric mobility may comprise applying an electric field and detecting the motion of at least one particle as function of the electric field so as to determine the electric mobility. It is an advantage of embodiments according to the present invention that accurate detection means can be used.

Detecting the motion of the particle may be performed by optically monitoring the motion of at least one particle.

Determining a particle property may comprise deriving a periodicity from the electric mobility distribution, and determining a property of a the particle based on a value representative for the periodicity of the electric mobility distribution.

The particle property may be any of a charge or a size.

The method may further comprise deriving a property of a liquid in which the particles are dispensed, based on the determined particle property.

The present invention also relates to a biosensing method for detecting a biological, chemical or bio-chemical event, the method comprising a method for determining particle properties as described above.

The present invention furthermore relates to a system for determining particle properties, the system may comprise a means adapted for determining an electric mobility distribution based on detection of individual particles and a means adapted for deriving a particle property based on a periodicity in the electric mobility distribution.

The means adapted for determining an electric mobility distribution may comprise an electric field generating means and a detection means adapted for detecting movement of at least one particle.

The present invention also relates to a biosensor for sensing a biological, chemical or biochemical event, the biosensor comprising a system as described above.

The present invention furthermore relates to a controller adapted for controlling operation of a system according to a method for determining particle properties as described above.

The present invention also relates to a computer program product adapted for, when executed on a computing device, performing a method for determining particle properties as described above. Furthermore it relates to a machine readable data storage device storing such a computer program product and/or the transmission thereof over a local or wide area telecommunications network.

It is an advantage of embodiments according to the present invention that methods and systems are provided allowing determination of electrical characteristics such as charge with a resolution of the elementary charge.

It is an advantage of embodiments according to the present invention that methods and systems are provided allowing to accurately determining and/or measuring extremely small electrical charges on particles, more particularly on colloidal particles.

It is an advantage of embodiments according to the present invention that methods and systems are provided allowing determination of particle size.

It is an advantage of embodiments according to the present invention that the methods and systems can be used for label-free detection of single molecules. The latter may allow insight in dynamics of molecular recognition. Also, accurate measurement of the elementary charge is easier on weakly charged colloidal particles. These weakly charged colloids such as nanoparticles or particles in a non-polar solvent are only being studied recently and are becoming increasingly important.

It is an advantage of embodiments according to the present invention that methods and systems can be provided allowing analysis and/or evaluation in real-time.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 11 is a table listing the resulting properties of $\mu_e \pm \sigma_{\mu e}$, a, $\sigma$, $\sigma_{\mu \neq}$ and $$\sqrt{\frac{1}{N}\sum_{i=1}^{N} Z_i^2}$$

Figure 1:
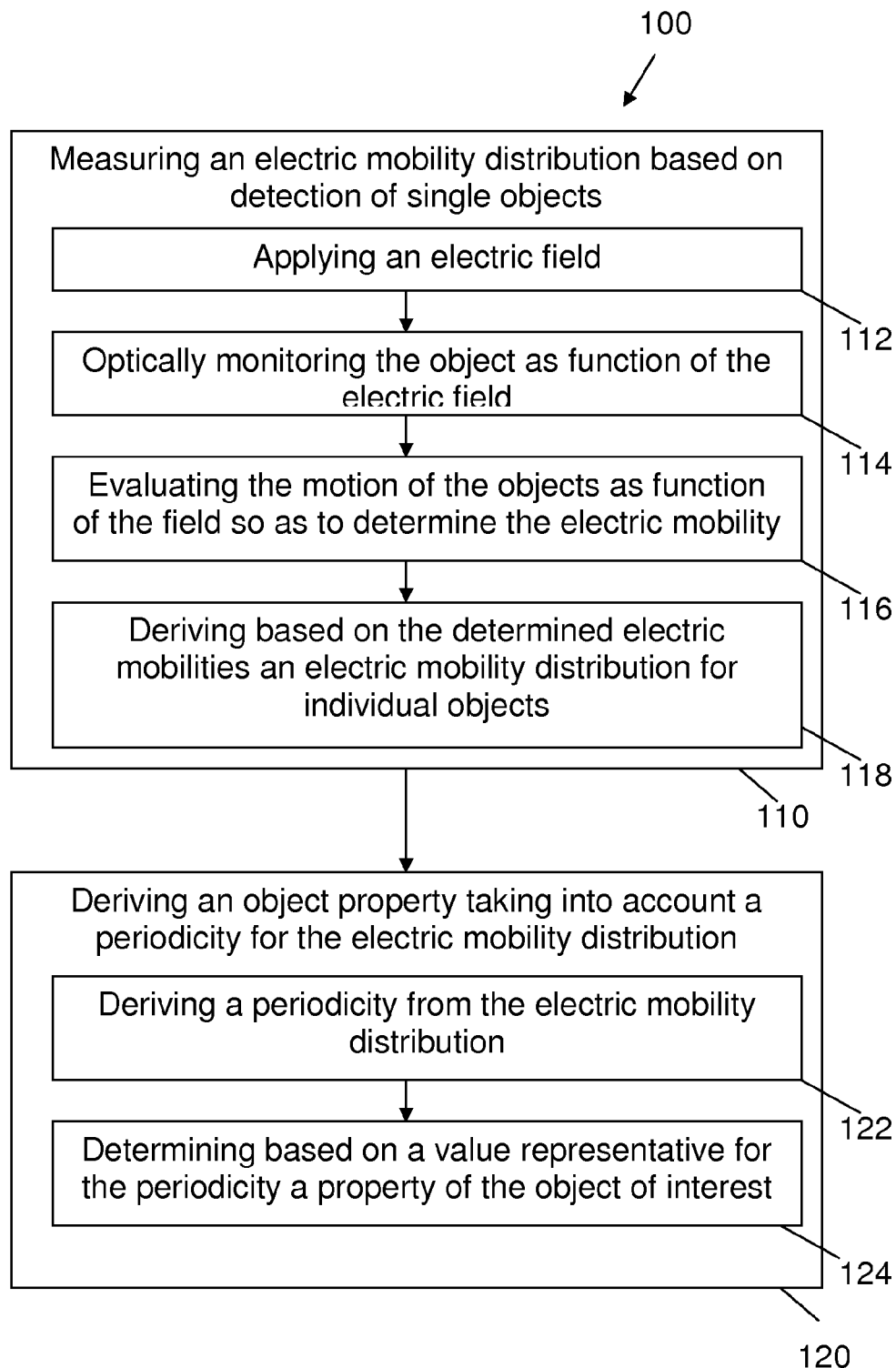
FIG. 1 is a schematic flow diagram of an exemplary method for determining particle properties according to an embodiment of the present invention.

for ten particles.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms are provided solely to aid in the understanding of the invention. With electrophoresis, in embodiments of the present invention, there is meant the electrokinetic phenomenon whereby particles dispersed in a fluid migrate under influence of an applied electric field. Such a phenomenon may occur because particles dispersed in a fluid nearly always carry some surface charge.

In embodiments according to the present invention, with colloidal particles there is meant particles occurring in a colloid. A colloid is a type of homogeneous mixtures consisting of at least two phases, i.e. a dispersed phase and a continuous phase, whereby the dispersed phase is made of tiny particles distributed throughout the continuous phase.

In embodiments according to the present invention with macromolecules there is meant molecules comprised of a number of atoms, e.g. more than 20 atoms or e.g. more than 50 atoms or e.g. more than 100 atoms, for example nucleotides, proteins, carbohydrates and lipids.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

In a first aspect, the present invention relates to a method for determining particle properties. Such a method may be performed to determine particle properties, such as for example size and/or electrical properties, but it may also allow determining other properties such as presence of particular components of interest, bound information such as e.g. binding dynamics, shape information, selectivity of particles, properties of the liquid such as e.g. the Debye length etc. Examples of an electrical property that may be determined may be charge and/or mobility, embodiments of the invention not being limited thereto. In one particular embodiment, the obtained particle property thus may be a characteristic size for the particle, e.g. a diameter or radius, cross section or volume. The method then may be based on determining a value for the elementary mobility of a particle, the elementary mobility being the mobility of a particle with the same size carrying the charge of one electron. The elementary mobility can be used to calculate an accurate value of the characteristic size. For example, the radius may be determined using the Stokes-Einstein relation. Depending on the particle charge, the electric field strength and the number of measurements the error on the radius can be well below 1%. In another particular embodiment according to the present invention, the obtained particle property is the mobility of a particle itself. Very small mobilities can be measured. In order to determine at least one particle property, the method according to embodiments of the present invention comprises measuring an electric mobility distribution based on the detection of single particles, i.e. individual particles. The particles may for example be colloidal particles, macromolecules, etc, the present invention not being limited thereto. The method is especially suitable for particles, e.g. particles like colloidal particles, with a small volume fraction. The method is for example especially suitable when particle concentrations of $10^{16}/m^3$ or lower are used. The size of the particles may be any suitable particle size that allows detection, e.g. optical detection. For example, when conventional microscopy is used, the particle size advantageously may be between 100 nm and several micrometers in radius. If more advanced detection techniques are used, the radius may even be smaller, e.g. below 100 nm when using laser aided techniques such as optical tweezing electrophoresis and quadrant detectors, or below 10 nm when fluorescence microscopy is used. The particles advantageously may be spherical in shape.

It is an advantage of embodiments according to the present invention that characterisation of particle properties in liquids can be obtained. Such liquids may be polar liquids or non-polar liquids. The liquids may be solvents. In some examples, the liquids are oil-based liquids or aqueous based liquids. Based on the measured electric mobility distribution, a particle property may be derived taking into account a periodicity of the electric mobility distribution.

By way of illustration, the present invention not being limited thereto, an exemplary method 100 for determining particle properties is provided in FIG. 1, indicating basic and optional method steps.

Prior to the standard steps of methods according to embodiments of the present invention, the method may comprise obtaining a colloid or dispersion of particles in a fluid, e.g. liquid, in order to be able to detect the electric mobility of the particles in the fluid, e.g. liquid. Obtaining such a dispersion may comprise preparing the dispersion or obtaining the dispersion from externally. Depending on the particular application, such obtaining may be performed in the process of running a biological, chemical or biochemical test. The dispersion of interest may stem from research or may be any type of dispersion for which particle properties need to be determined.

In a first step, the method comprises measuring 110 an electric mobility distribution based on detection of single particles, e.g. colloidal particles or macromolecules. Measuring an electric mobility distribution may be performed in a plurality of ways. The electric mobility distribution obtained may correspond with the distribution of the electric mobility of single particles, e.g. individual particles. It may be determined by determining for one particle a plurality of electric mobilities in subsequent measurements, i.e. over time, by determining for a plurality of particles the electric mobility simultaneously but in a distinct manner, or by a combination thereof. Determining the electric mobility for a plurality of particles simultaneously but in a distinct manner thereby may mean that the electric mobility is determined for each individual particle separately, but that this is done for a number of particles at the same moment in time of the experiment. Determining the electric mobility of particles may for example be performed by performing for example electrophoresis experiments. In some embodiments according to the present invention, the electric mobility of particles may be determined by applying an electric field, e.g. an alternating electric field, as indicated in step 112, optically monitoring the particle, as indicated in step 114, and by evaluating the motion as function of an applied electric field, as indicated in step 116, so as to determine the electric mobility. Determining the mobility of individual particles may for example be performed by measuring the particle velocity during the application of the electric field. The latter may for example be performed in an electrophoresis cell, although the invention is not limited thereto. Measuring 110 an electric mobility thus may comprise optical detection, e.g. imaging, single particles, e.g. individual particles. Such optical detection, e.g. imaging, may be based on any suitable optical detection technique. The number of measurement results for electric mobility required may be sufficient that at least a rough distribution in the electric mobility is visible and is determined at the upper side by the amount of measurement time available and by the required accuracy. The number of electric mobility values that may be obtained may for example be between 10 and 10000, e.g. between 50 and 5000, or e.g. between 50 and 500. The method may comprise obtaining an electric mobility distribution for an individual particle based on the measured electric mobility, as indicated in step 118. In one embodiment, the present invention relates to a method for determining particle properties as described above, whereby the particles to be studied are visualised using fluorescence microscopy. The latter has the advantage that the observation of the particles is less limited to the size of the particles, as optical microscopic observation may be restricted, e.g. to particles of about one hundred nanometer. By using fluorescence microscopy, smaller particles, e.g. single molecules, may be studied. Excitation may for example be performed using laser light. Also other types of optical detection may be used such as for example dark field microscopy, imaging using a detector, e.g. a CCD camera, detection with a quadrant detector, whereby for example use can be made of laser trapping, detection using a photodiode, detection in an optical interference region, etc. By introducing an optical or an electrical force field to trap particles in a confined region, particles can be measured for longer periods of time (minutes, hours) and they can remain trapped when a reagens is added. Optical trapping is often used in combination with a quadrant detector for fast determination of the position of the particle. Other non-optical techniques also may be used, such as for example acoustophoresis in which the particle motion in an electric field results in a transfer of momentum to the liquid and to the development of an acoustic wave.

The particles charge in experiments changes in time. Advantageously, the characteristic time at which the charge changes should be smaller than the total duration of the experiment, but larger than the time for a single mobility measurement. In this way the probability of the charge changing during that mobility measurement may be reduced or minimized. The timing and duration of the electric mobility measurement may be determined based on the expected timing for the charge changes.

In a second step 120, methods of the present invention comprise determining a particle property based on a periodicity present in the electric mobility distribution. The periodicity in the electric mobility distribution may be based on the change or altering of the number of elementary charges present on the particle, e.g. on the surface of the particle. The periodicity may be caused by jumps over a value $\mu_e$, corresponding with the difference in mobility when the particle charge reduces or increases with a single elementary charge. Such jumps may occur because a particle alters its charge over time while migrating in an electric field and/or by the fact that different particles may have a different surface charge. The periodicity in the electric mobility distribution may be characteristic for an electrical characteristic $\mu_e$, which can be used for deriving therefrom characteristics of the particles under study such as charge or size. Once $\mu_e$ is known the charge can be determined by deriving the number of elementary charges that are present on the particle, using for example $$Z_i \cong \mu_i/\mu_e$$

Accurate estimations can be made of the particle radius a using for example the Stokes-Einstein equation in the case that the Debye length ($1/\kappa$) is much larger than the particle size $$\mu_e = e/6\pi\eta a$$

where $\eta$ is the viscosity of the liquid, or for example using a more general expression such as the Hückel-Onsager equation when $1/\kappa$ is larger than a or the Helmholtz-Smoluchowski equation in case that $1/\kappa$ is smaller than a. The diffusion constant D of the particle can be estimated using for example the Einstein equation $$D = \mu_e kT/e$$

using the Einstein relation with k the Boltzmann constant and T the absolute temperature.

Determination of the particle properties thus may for example be based on the above or related theoretical formulas, based on look up tables previously determined for this type of measurements, based on a neural network, based on predetermined algorithms, etc. By way of example, the present invention not being limited thereto, determination of particle properties based on theoretical assessment will be described further below. Thus, in the present step, the method may comprise deriving a periodicity from the electric mobility distribution, as indicated in step 122, and determining based on a value representative for the periodicity a property of the particle of interest, as indicated in step 124. The frequency with which certain particle properties change can be determined from the calculated values of the particle properties as a function of time, for example the frequency with which the particle charge changes.

The error on the determined mobility values is due to Brownian motion (usually the most important), hydrodynamic instabilities and other measurement errors. The standard deviation ($\sigma_\mu$) for the measured electrophoretic mobility values can be estimated as the average error due to Brownian motion:

$$\sigma_\mu = \frac{1}{E}\sqrt{\frac{2D}{\Delta t}}$$

which is the ratio of the mean displacement in one dimension due to Brownian motion $\sqrt{2D\Delta t}$ over the field induced motion $\mu E \Delta t$, multiplied with $\mu$. Here D represents the self-diffusion constant of the particle, E is the electrical field, $\mu$ is the electric mobility of the particle and $\Delta t$ is the time of one speed measurement. In particular embodiments according to the present invention, the effect of errors, e.g. Brownian motion, on the mobility measurements may be reduced. The latter means that the standard deviation $\rho_\mu$ of the electric mobility $\mu$ can be reduced with respect to its value. Such a reduction in error may for example be achieved by using a longer measurement time $\Delta t$ and/or by increasing the applied electric field E. The scattering due to hydrodynamic instabilities can be minimized by avoiding electrochemistry. The field induced motion of the particles should be such that the scattering on the determined mobility measurement is small compared to the mobility of a particle of the same size with charge equal to the unit charge e. In this case a discrete variation can be observed in the mobility data, which corresponds to discrete changes in the charge of the particle. This mechanism allows to find the discrete charge in different time intervals with high confidence level (for example above 99%), and as a consequence the elementary mobility of the particle.

As hydrodynamic flows can complicate the detection of discrete mobilities, in an advantageous embodiment hydrodynamics is avoided by limiting the applied voltage to about 100 V and/or by using a liquid medium of low electrochemical activity and low ionic strength and/or by limiting the dimensions of the container of the liquid.

By way of illustration, the present invention not being limited thereto and not being bound by the underlying theory, an exemplary illustration of a detailed analysis of multiple mobility measurements yielding highly accurate values of particle size and particle charge as function of time will be provided, the method taking advantage of the discrete nature of the electric charge and the known value of the unit charge. Embodiments of the present invention thereby advantageously provide electric property results without the need for using the Stokes Einstein equation. This is advantageous as in many cases the particle size is not accurately known or even not known at all. Furthermore the accuracy of a mobility measurement is inherently limited by the Brownian motion. These two factors strongly influence the accuracy of results obtained with the Stokes Einstein equation.

For determining an electric mobility distribution based on measured electric mobility of individual particles, the electric mobility may be determined for a plurality of particles or the electric mobility of a particle may be determined a plurality of times. The latter thus may result in a plurality of mobility values, e.g. N mobility values $\mu_i$ (with i:1 ... N) from a particle with radius a which can be modelled as $$\mu_i = Z_i \mu_e + \in_i$$

wherein $Z_i$ are integers representing the discrete charge in units of the elementary charge e, $\mu_e$ is the elementary mobility of a particle with radius a and charge e and $\in_i$ is the error on the measurement. It could be assumed that the error $\in_i$ due to Brownian motion or measurement limitations is uncorrelated and normally distributed, with average 0 and variance $\sigma^2$. From the electric mobility distribution, the elementary mobility $\mu_e$, the variance on the error $\sigma^2$, the particle size a and/or the diffusion constant D may be derived. If the error $\in_i$ and the standard deviation $\sigma$ thereon are small compared to the elementary mobility $\mu_e$, the mobility values $\mu_i$ are clustered around multiples of the elementary mobility $\mu_e$. If the condition $\in_i \ll \mu_i$ is fulfilled, the number of charges is given by $$Z_i \approx \mu_i/\mu_e$$

and since $Z_i$ is an integer, this result can be rounded to the nearest integer, i.e. $Z_i = [\mu_i/\mu_e]$ where the brackets mean rounding to the nearest integer. The following equation can be derived $$\mu_i - [\mu_i/\mu_e]\mu_e = \in_i \ll \mu_e$$

The function $R^2(\mu)$ can be evaluated which is the sum of squares of the residuals $\in_i$ where the unknown value of $\mu_e$ is replaced by $\mu$:

$$R^2(\mu) = \sum_{i=1}^{N}(\mu_i - [\mu_i/\mu]\mu)^2$$

For completely random mobility data $R^2(\mu)$ has an expectancy $N\mu^2/12$. If the mobility data is clustered around multiples of $\mu_e$, we expect $R^2(\mu)$ to be significantly smaller than $N\mu^2/12$ for the value of $\mu_e$. Therefore the elementary mobility $\mu_e$ should correspond to a local minimum in $R^2(\mu)$.

Once $\mu_e$ is known, accurate estimations can be made of the particle radius, for example using $\mu_e = e/6\pi\eta a$ or related expressions, and the diffusion constant $D = \mu_e kT/e$ using the Stokes and Einstein relations with k the Boltzmann constant and T the absolute temperature. Each measured mobility $\mu_i$ corresponds to an estimation of a number of elementary charges, which is in general not an integer, due to the measurement error in $\mu_i$. Since the charge is a multiple of the elementary charge, we find the most probable value of Z by rounding to the nearest integer $Z_i = [\mu_i/\mu_e]$. For particles with given standard deviation of the mobility $\sigma$ the fraction of correctly estimated values is given by $$erf(\mu_e/\sqrt{8}\sigma).$$

The variance of the residual mobility is calculated as $$\sigma^2 = \Sigma(\mu_i - Z_i\mu_e)^2/(N-1)$$

Analysis of the error on $\mu_e$ and the calculated properties that are derived from it is quite complicated and depends on the values $Z_i$ and $\sigma/\mu_e$. In the theoretical limit $\sigma/\mu_e \ll 1$ the overlap between the peaks in the mobility histogram is negligible and the charge is always estimated correctly. In this case, the variance $\sigma^2_{\mu e}$ can simply be obtained using the $(Z_i, \mu_1)$ data and standard linear regression theory $$\sigma^2_{\mu_e} = \sigma^2 \Big/ \sum_i Z_i^2$$

According to embodiments of the present invention, the accuracy of the method can be optimised by increasing the number of measurements per particle and/or by minimising the error of a single mobility measurement. The latter may be obtained by using a longer measurement time $\Delta t$ and/or using a higher electrical field E and/or using smaller particles.

Figure 2:
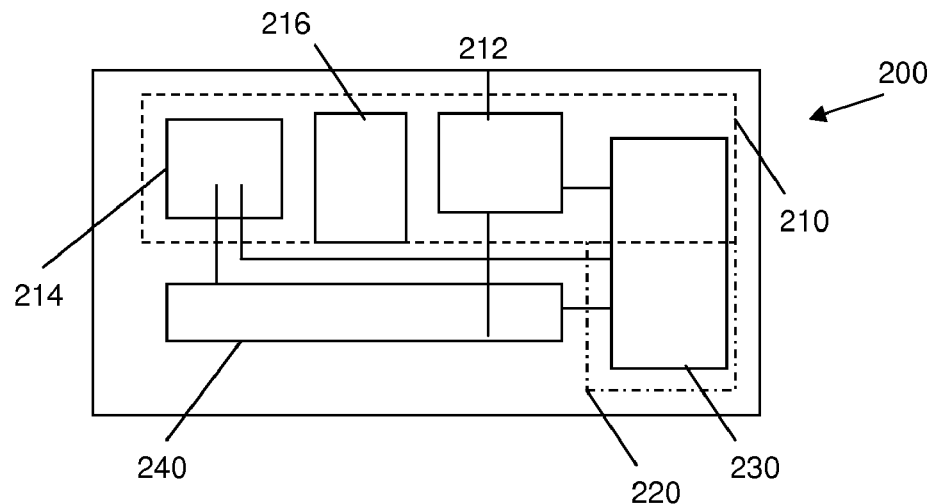
FIG. 2 is a schematic representation of a system for determining particle properties according to an embodiment of the present invention.

In a second aspect, the present invention relates to a system for determining properties of an particle, such as for example the mobility, the charge or the size of an particle or properties related thereto but also binding properties of the particles, presence of other elements bound to the particles, embodiments of the present invention not being limited thereto. Such a system may for example be part of a sensor, e.g. a biosensor, where it may assist in detecting a biological, biochemical or chemical event, although the invention is not limited thereto. The system for determining properties of an particle is based on an ability to measure a distribution of the electric mobility of particles and to derive therefrom an particle property. The system advantageously may be adapted for performing the method according to the first aspect. By way of illustration, the invention not being limited thereto, an exemplary system is shown in FIG. 2, indicating standard and optional components. The system 200 for determining particle properties comprises a means 210 for determining an electric mobility distribution and a means for 220 deriving from a periodicity in the electric mobility distribution a property of the particle under study, a frequency of change of a particle property etc. ... Both components may be implemented in software as well as in hardware. These means may comprise processing power for performing the required processing. The processing power may for the means 210 for determining an electric mobility distribution and the means 220 for determining an particle property use processing capacity of the same or distinct processors 230. The means 210 for determining an electric mobility distribution may comprise hardware components assisting in or allowing determination of electric mobility of individual particles, although the latter may be provided externally and the means for determining an electric mobility distribution may take as input electric mobility measurements for individual particles. The means for determining an electric mobility distribution thus may function by deriving an electric mobility distribution for individual particles. The latter may be based on input data for a plurality of electric mobility values for a single particle, electric mobility values for a plurality of different particles or a combination thereof. The data thereby may be such that each electric mobility value corresponds with the electric mobility of a single particle. In case the means for determining an electric mobility distribution 210 comprises hardware for determining an electric mobility value of an individual particle, the latter may be implemented as an electric field generating means 212, a detection system 214 for monitoring the position or evaluating the motion of an particle, and a sample compartment 216 for providing the sample such that it is influenced by the electric field and the position of the particles can be monitored. The system may be implemented as an electrophoretic cell. By way of example, an electrophoretic cell may be used with a small electrode spacing, so that high electrical fields, e.g. in the order of $10^6$ V/m, can be achieved with relatively small voltages (e.g. below 100 V). An advantage of low applied voltages is that undesired electrochemical redox reactions at the electrodes and electrohydrodynamic instabilities are avoided. The system furthermore may comprise a controller 240 for controlling the electric field generating means 212 and the detection system 214. Such a controller may be included or separate from the system and is in more detail described in a further aspect. Other optional components such as for example an input means, an output means, etc. also may be present. Furthermore components having the functionality of the different method steps or sub-steps as described in the methods of the first aspect may also be present.

In a third aspect, the present invention relates to a detection system for detecting particle properties, such as for example a biosensor or sensor for determining biological, chemical or bio-chemical events. The detection system may comprise a system for determining properties of an particle as described in the second aspect, the detection system comprising the same features and advantageous as set out in the second aspect.

In a fourth aspect, the present invention also relates to a controller for controlling a system for obtaining particle information according to the second aspect or for controlling different method steps in a method for determining particle information according to the first aspect. Such a controller may provide control signals for controlling an information determining system for determining properties of particles. The controller may for example provide control signals for measuring an electric mobility distribution based on the detection of single particles, i.e. individual particles. The controller may be adapted for controlling an optical detection system and an electric field generating means. The controller may be adapted for synchronising the optical detecting and the application of the electric field. The controller furthermore may be adapted for controlling functions of the processing means for determining an electric mobility distribution, deriving data and/or determining particle properties, by providing appropriate control signals and/or appropriate data signals from the optical detection means and/or the electric field generating means. The controller furthermore may be adapted for controlling a measurement and/or data processing system according to methods for determining particle properties as described in the first aspect. Control signals for controlling the different standard and optional steps thus may be provided. The controller may be software based or hardware based. When the controller is hardware based, the controller may be implemented using for example FPGA technology or ASIC technology.

Figure 3:
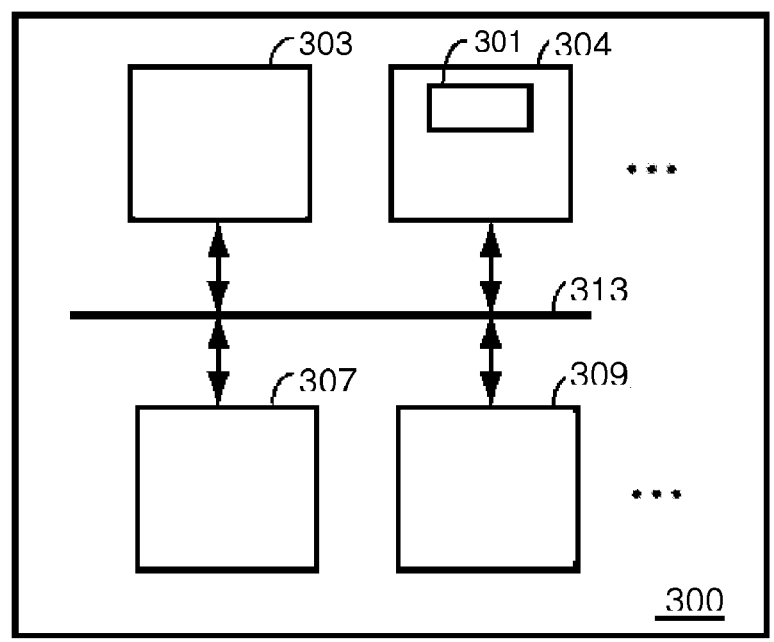
FIG. 3 is a schematic representation of a processing system that is adapted for performing a method for determining particle properties according to an embodiment of the present invention.

The above-described method embodiments and/or controller or method for controlling of the present invention may be implemented in a processing system 300 such as shown in FIG. 3. FIG. 3 shows one configuration of processing system 300 that includes at least one programmable processor 303 coupled to a memory subsystem 305 that includes at least one form of memory, e.g., RAM, ROM, and so forth. It is to be noted that the processor 303 or processors may be a general purpose, or a special purpose processor, and may be for inclusion in a device, e.g., a chip that has other components that perform other functions. Thus, one or more aspects of the present invention can be implemented in digital electronic circuitry, or in computer hardware, firmware, software, or in combinations of them. The processing system may include a storage subsystem 307 that has at least one disk drive and/or CD-ROM drive and/or DVD drive. In some implementations, a display system, a keyboard, and a pointing device may be included as part of a user interface subsystem 309 to provide for a user to manually input information. Ports for inputting and outputting data also may be included. More elements such as network connections, interfaces to various devices, and so forth, may be included, but are not illustrated in FIG. 3. The various elements of the processing system 300 may be coupled in various ways, including via a bus subsystem 313 shown in FIG. 3 for simplicity as a single bus, but will be understood to those in the art to include a system of at least one bus. The memory of the memory subsystem 305 may at some time hold part or all (in either case shown as 311) of a set of instructions that when executed on the processing system 300 implement the steps of the method embodiments described herein. Thus, while a processing system 300 such as shown in FIG. 3 is prior art, a system that includes the instructions to implement aspects of the methods for determining properties of particles is not prior art, and therefore FIG. 3 is not labelled as prior art.

The present invention also includes a computer program product which provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fiber optics, including the wires that comprise a bus within a computer.

As indicated above, it is an advantage of embodiments according to the present invention that charge, mobility, size or other related properties, e.g. derived quantities, can be determined accurately for single, i.e. individual, particles, such as for example colloidal particles or macromolecules. The property thereby may be varied in time. It is an advantage of embodiments according to the present invention that the methods can be used for a variety of applications. By way of illustration, some examples are described below, the invention not being limited thereto.

In a first exemplary application, the methods and systems according to embodiments of the present invention may be used for the detection of small quantities of target molecules that bind in a specific way to receptors, e.g. small particles, which can be made visible under a microscope. In other words, visibility of these particles may be performed using optical techniques as described above. As binding of target molecules on the particles gives rise to a variation in charge or in size, the latter results in a detection of the target molecules present. Some, non limiting examples of such an application is detection or measurement of the presence or quantity of heavy metal-ions, detection of DNA, detection of proteins, detection of enzymes, etc. It is an advantage of such applications that detection can be performed in an accurate manner. In some embodiments, labelling of the target molecules or receptors may be performed for detection, whereas in other embodiments a label-free detection may be obtained. For example, in one embodiment, the target molecules do not comprise a fluorescent label. Specificity of the binding may be induced by positioning receptors on a surface, e.g. antibodies, which specifically bind to the target molecules of interest. One example of an application of detecting particle properties in biological detection is the detection of an particle, e.g. nanoparticle, coated with antibodies. Detection may for example be performed before and after adding of biomolecules and in this way, the presence of certain biomolecules can be detected if the reaction with the antibody causes a change in the charge and/or size of the nanoparticle. The latter may allow measurements of single molecule reactions.

In a second exemplary application, the methods and systems according to embodiments of the present invention may be used for the detection of molecules, such as for example DNA or proteins, which can be made visible with an optical system, e.g. a microscope. The latter may for example be obtained using fluorescent labels that bind to the molecules.

In a third exemplary application, the methods and systems according to embodiments of the present invention may be used for study and/or analysis of bounds, e.g. the dynamics of bounds, of atoms or molecules on the surface of a detectable particle. Individual reactions that have an influence on the charge or size can be detected, resulting in an accurate and/or high resolution technique.

In a fourth exemplary application, the methods and systems according to embodiments of the present invention may be used for determining the size of charged colloidal particles. The latter may be performed in real-time. Such methods may comprise determining the adsorption and/or dissociation of molecules on an particle.

In a fifth exemplary application, the method and systems according to embodiments of the present invention may be used for determining the charge of particles, e.g. colloidal particles. Determining may be performed in real-time. The latter may allow study and analysis of mechanisms of charging of particles, e.g. colloidal particles. In one example, the charging dynamics of particles may be monitored, whereby it is possible to measure the discrete charge of an particle, e.g. colloidal particle in time. The latter may for example be used to analyse chemical reactions at the particle surface, although applications are not limited thereto. Accurate measurement of charge and size distributions may also be useful in the analysis of nanoparticles.

In a sixth exemplary application, the methods and systems according to embodiments of the present invention may be used for lab-on-chip analysis or detection applications, e.g. for single particle analysis. Such applications may be used in the biological, chemical or biochemical analysis field.

In a seventh exemplary application, the methods and systems according to embodiments of the present invention may be used for calibration testing of electrophoretic measurement devices. The latter may allow to bring systems in agreement with predetermined standards. One standard to which systems may be made compliant is for example the NIST 1980 mobility standard.

In an eighth exemplary application, the methods and systems according to embodiments of the present invention may be used for determining properties of inks. Such characterisation may allow better control of ink properties, thus allowing creation of better inks or better selection of inks depending on the application of the ink envisaged.

By way of illustration, the present invention not being limited thereto, an example of some experimental results is provided.

Figure 4A:
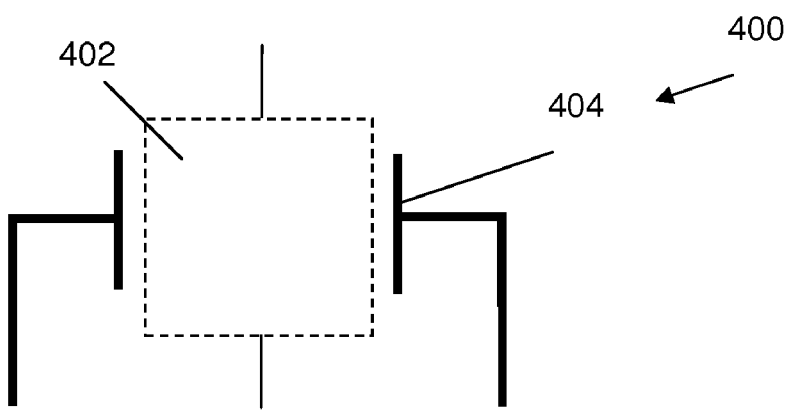
FIG. 4a is a schematic representation of an electrophoretic cell, as can be used in embodiments according to the present invention.
Figure 4B:
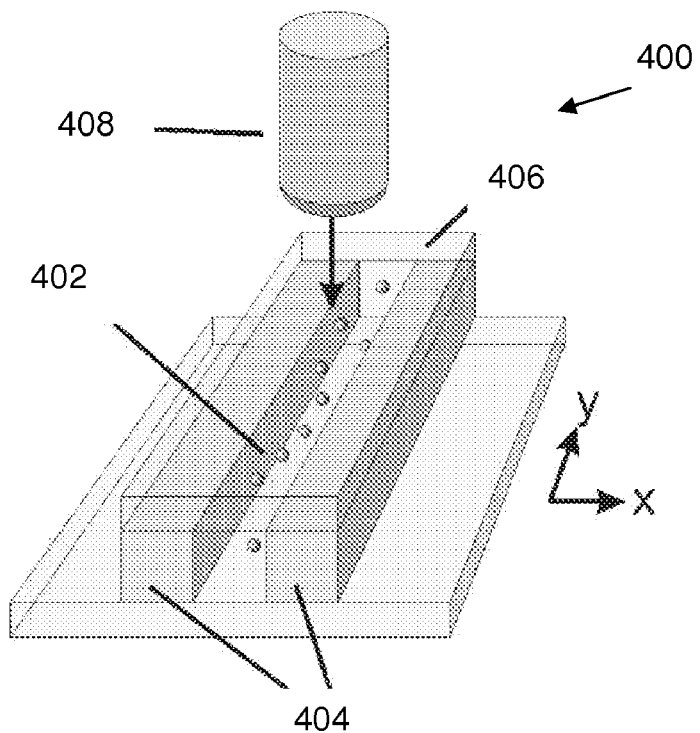
FIG. 4b is a schematic representation of an electrophoretic cell that is useful for particle suspensions in nonconductive liquids.
Figure 4C:
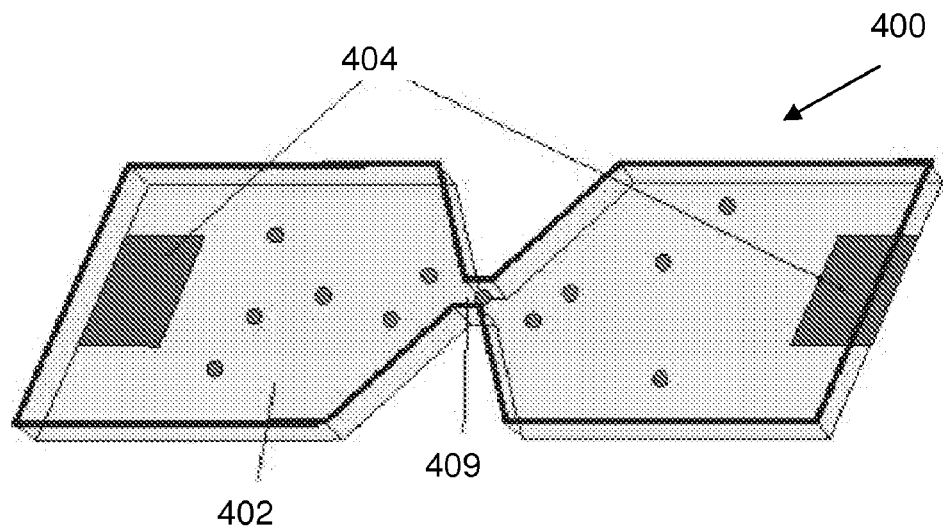
FIG. 4c is a schematic representation of an electrophoretic cell that is useful for particle suspensions in conductive liquids.
Figure 4D:
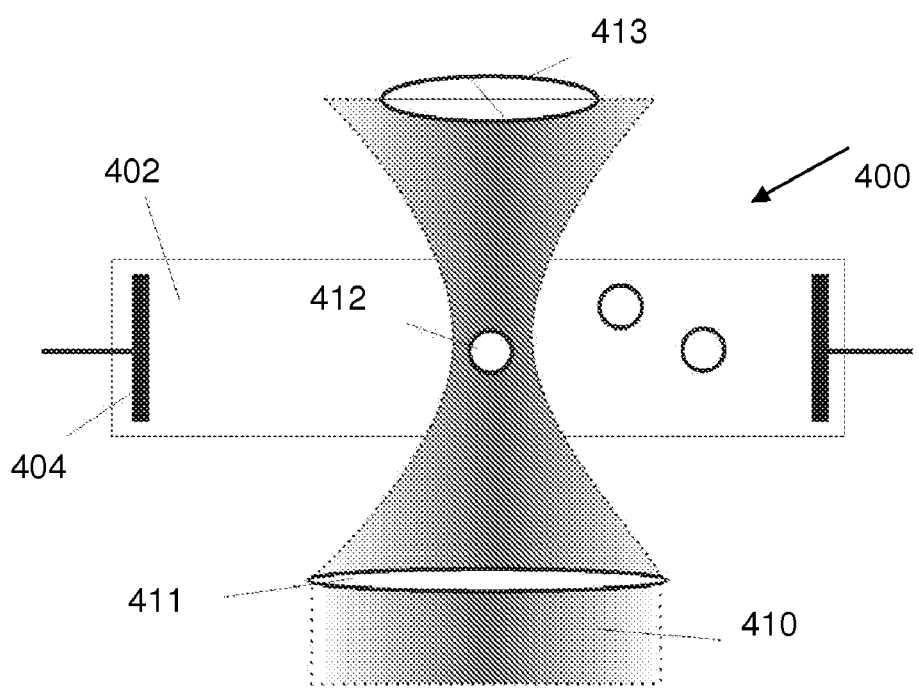
FIG. 4d is a schematic representation of an electrophoretic cell with means for optical trapping of particles.

In these experiments, electrophoretic cells were used as shown schematically in FIG. 4a and in FIG. 4b, in FIG. 4c and in FIG. 4d. FIG. 4a indicates a schematic representation of an electrophoretic cell 400 comprising a specimen volume 402 containing a liquid and particles, possibly connected by an input and an output, and a set of electrodes 404 (in the present example being two electrodes) to apply a voltage and to generate a field in the liquid. The dimensions of the electrodes in the present example are 600 μm×600 μm×1 cm, embodiments of the present invention not being limited thereby. The distance between the electrodes in the present example is 100 μm. The electric field between the electrodes is approximately homogeneous. This geometry is especially interesting for use with non-conductive liquids, such as non-polar liquids. FIG. 4b indicates an example of an electrophoretic cell 400 showing 2 electrodes 404, cover glasses 406 and a specimen volume 402 comprising a liquid containing particles. Other optional features such as for example an objective 408 and translation stage (not shown) may be present in such a setup. Imaging and processing was based on a standard particle tracking setup and image analysis method. The optical system used comprises a microscope, whereby a 50× objective magnification was obtained, and a digital CCD camera with a total optical magnification of 196.5 nm per pixel on the CCD camera. Image capturing was performed using a framegrabber to capture the images on a personal computer. FIG. 4c indicates a schematic representation of an electrophoretic cell 400 which is useful for example for conductive liquids, such as polar liquids. The electrophoretic cell 400 contains liquid with particles 402 and electrodes 404. The electrophoretic cell contains a channel 409 over which a large fraction of the applied voltage drops, and in which large electric fields are obtained. Since larger electrical fields are advantageous for the accuracy of the electrophoretic measurement, it is beneficial to measure properties of particles located in the channel. The dimensions of the liquid volume near the electrodes are for example 1 cm×1 cm×100 μm (length×width×height), while the channel dimensions are for example maximally 250 μm×250 μm×250 μm, advantageously maximally 100 μm×100 μm×100 μm. For polar liquids, advantageously, all of the dimensions of the channel over which an electric field is placed advantageously are smaller than 250 μm, advantageously smaller than 150 μm. FIG. 4d. shows a schematic representation of an electrophoretic cell 400 containing liquid with particles 402 and electrodes 404. An optical trapping setup is used to trap for example a single particle using a gradient in the optical intensity. A laser beam 410 is focused using lenses 411. A particle 412 is trapped in the focus of the laser. The random Brownian motion of the particle is reduced by the optical trap. A detector is used to monitor the particle position, for example a CCD camera or a quadrant detector 413. When an electric field is generated, an additional force is applied on the particle, and the particle mobility can be measured from the particle motion in an electric field.

In the first example, silica spheres were used as colloidal particles and particles were characterised, illustrating some advantages and possibilities of the above described methods and systems. An electrophoretic cell as in FIG. 4a and FIG. 4b was used. The silica spheres were as obtained from Mo-Sci corporation and had a radius 1.05 μm±0.05 μm (mean±standard deviation). The particles were not treated further. They were dispersed in high purity dodecane (dodecane Rectapur, as obtainable from VWR). The fluid was chosen as the liquid medium for its low dielectric constant ($\in=2$) to avoid hydrodynamics caused by electrochemistry at the electrodes. The particle concentration used was approximately $10^{15}$ m$^{-3}$. The technique used for measuring the electric mobility distribution based on detection of single particles was video micro-electrophoresis.

In the present example, electrodes in the electrophoretic cell were driven using a wave generator and a voltage amplifier (10×). The applied wave form was a square wave voltage with amplitude of 100V and a frequency of 2 Hz. The electrodes used were parallel electrodes with a spacing d. The spacing was chosen to be small in the present example, so that high fields could be achieved while only small voltages were needed (in the present example being a spacing of 80 μm and a voltage of 100V, resulting in a field of about $10^6$ V/m). The amplitude of the electric field E then is determined as $$E=V/d$$

In the present example, distances are measured in number of pixels on the image, and thus the distance d can be determined as the number of pixels between the electrodes.

At the rising edge of the square wave voltage the image acquisition is triggered to ensure identical conditions for each experiment and images are taken at 20 Hz (0.05 s intervals). Each particle is measured during about 30 seconds, resulting in 600 images. For each half period of the square voltage the particle velocity was calculated as:

$$v_i=\Delta x_i/\Delta t$$

with $\Delta t=0.15$ s.

During each half period of the square wave voltage, the electrophoretic mobility μ of the particle was determined as its speed in the direction of the field divided by the amplitude of the electrical field $$\mu_i=v_i/E.$$

Figure 5:
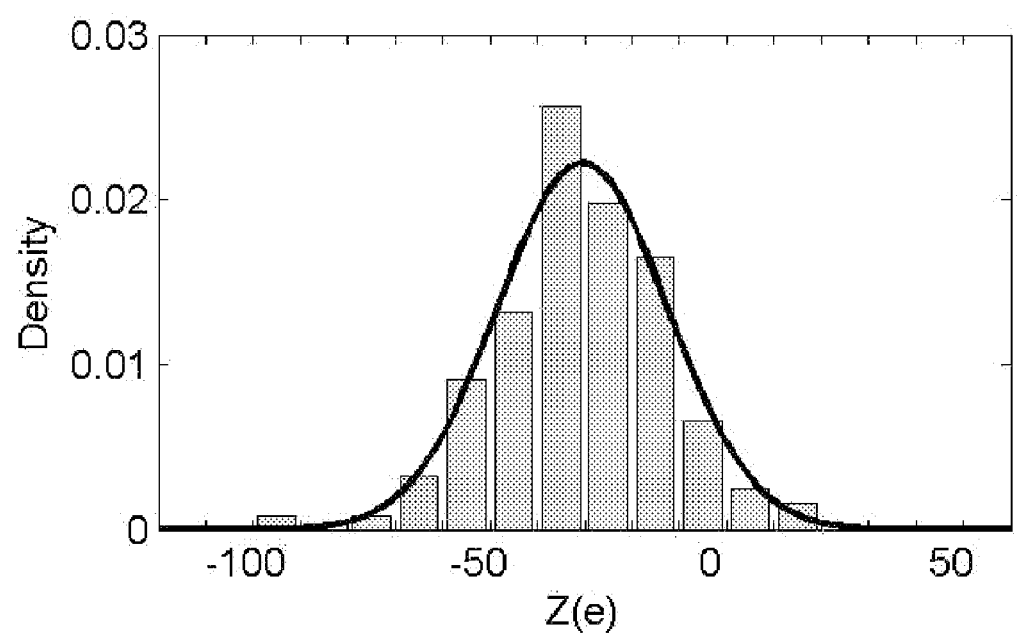
FIG. 5 is a low resolution charge histogram indicating the range of particle charges during different mobility measurements, as can be used in embodiments according to the present invention.

Due to the low dielectric constant, in the present example being $\in=2$, free charges are associated with a high electrostatic energy and ions require a lot of energy to separate from the particle surface. As a result, the charge of silica particles is low. For 120 particles, the charge determined by electrophoretic measurement was in the range between −70 e and +20 e, with e the elementary charge. The latter is illustrated by way of example in FIG. 5. The measured charges are more than 100 times smaller than the charge in water having a dielectric constant of about 80.

Figure 6:
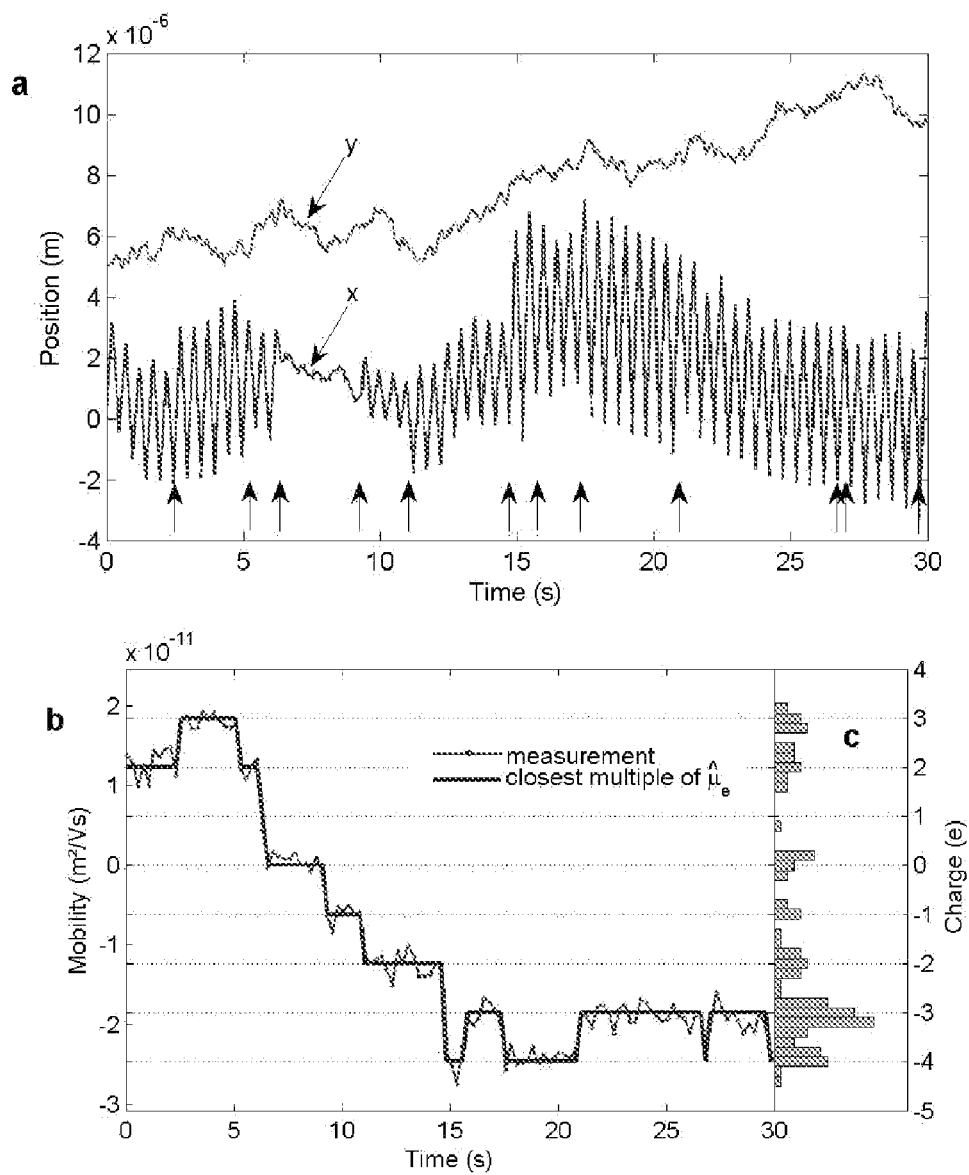
FIG. 6 is an example of an electrophoretic measurement on a silica particle in dodecane, indicating the position as function of time (a) and the mobility as function of time (b), and the mobility distribution (c), as can be used in a method according to an embodiment of the present invention.

As indicated above the individual particles are tracked in time while they are moving in an electric field generated by applying a square wave voltage. As a result the particle position measured along the field as a function of time has roughly a triangular shape, with the amplitude proportional to the charge. The latter is shown by way of illustration in FIG. 6. The position as function of time is shown in part (a), whereas the mobility as function of time is shown in part (b). The distribution of the mobility is shown in part (c). The position perpendicular to the field is governed by Brownian motion. The amplitude of the electrical field is about $10^6$V/m. Typically a plurality of values, e.g. 120 values, of the electrophoretic mobility are calculated for each particle over a period of 30 seconds. The latter is also illustrated by way of example in FIG. 6. By way of comparison, an exemplary model for determining the electrophoretic mobility for spherical particles with an electrical charge Z based on the Stokes-Einstein relation can be used, which is valid in the present case because the Debye length (~15 μm) is much larger than the particle size (~1 μm). Such a model provides an electrophoretic mobility given by $$\mu = Ze/6\pi\eta a$$

In the present example, based on the exemplary model described above, with a known radius of $a=1.05$ μm and a viscosity of the solvent $\eta$ of $1.38\times10^{-3}$ Pa s, a mobility $\mu$ of about $6.10^{-12}$ m$^2$V$^{-1}$s$^{-1}$ for a particle carrying a unit charge was obtained. From the obtained experimental results, it can be seen that the mobility determined with the model agrees well with the distance between the peaks in the experimental histogram of the electrophoretic mobility. This illustrates features and advantages of the method and system embodiments as described above. The peaks in the mobility histogram indicate that the particle charge Z varied in discrete steps during the measurement and confirm that elementary charge is resolved.

Figure 7:
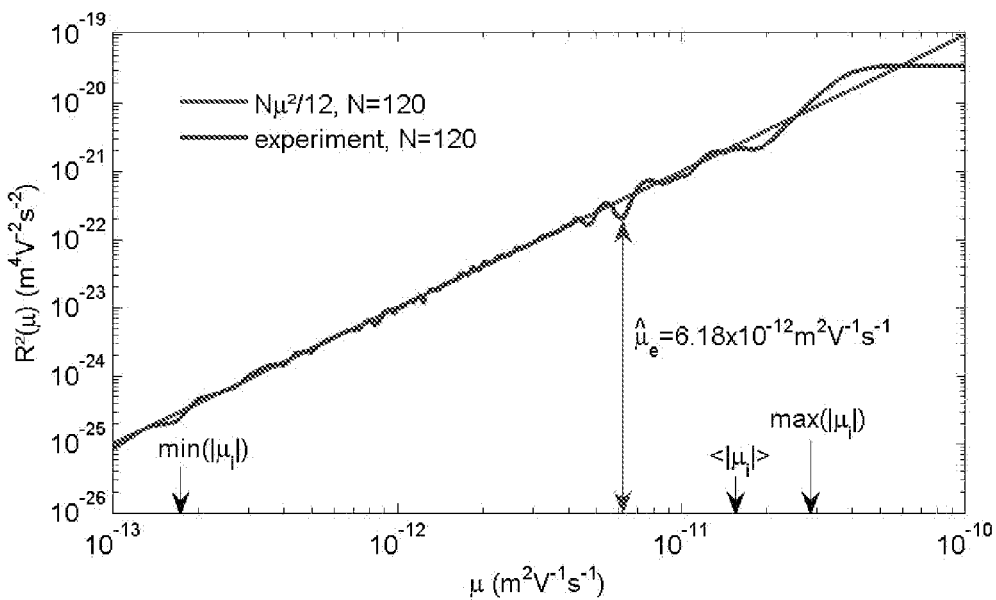
FIG. 7 is an example of an analysis of the electrophoretic mobility for deriving a best estimate elemental mobility $\mu_e$, as can be used according to embodiments of the present invention.

For the present example, a full determination of properties based on but not limited to the theoretical aspects as set out above was performed. In FIG. 7 the obtained regression function $R^2(\mu)$ is shown using the mobilities from FIG. 5 part (b) with N=120. For this experiment we find $\mu_e=6.18\times10^{-12}$ m$^2$V$^{-1}$s$^{-1}$ and the error is only about $0.05\times10^{-12}$ m$^2$V$^{-1}$s$^{-1}$. In the present experiment the fraction of determined charge that does correspond with the actual charge was 98% (for 2% of the estimations the error is one unit and the estimated number of charges thus is the actual number of charges±1).

Figure 8:
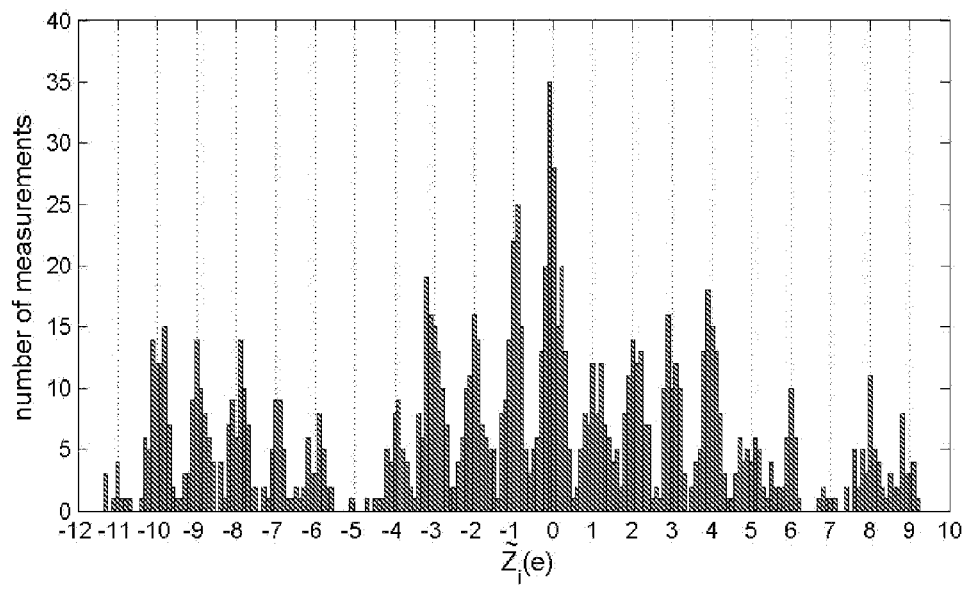
FIG. 8 is a schematic representation of a charge histogram as can be obtained based on a plurality of electrophoretic measurements and can be used in a method according to an embodiment of the present invention.

The histogram in FIG. 8 was obtained by using the 1200 values of $Z_i = \mu_i/\mu_e$ for 10 particles, where $\mu_e$ is the value determined for the corresponding particle. It illustrates the clustering of data around whole numbers, as, in the present example, the charge varies between −12 e and +10 e.

In the above experiments provided by way of illustration, the typical value of $\sigma/\mu_e$ was 0.21, which is not negligible compared to 1. Therefore it was not possible to determine the variance on $\mu_e$ using standard linear regression theory. An estimation of the variance on $\mu_e$ (denoted $\sigma^2_{\mu e}$) with 100 sets of randomly generated mobility data (also containing 120 values per series) according to the normal distribution $N(Z_i, \mu_e, \sigma^2)$ is determined, using the estimated values of $\mu_e$, $Z_i$ and $\sigma$. The standard deviation of the 100 values of the elementary mobility obtained in this way is defined as $\sigma_{\mu e}$. Typical values for $\sigma_{\mu e}/\mu_e$ are between 0.2% and 2%.

By way of illustration, the present invention not being limited, obtained resulting properties $\mu_e \pm \sigma_{\mu e}$, a, $\sigma$, $\sigma_\mu$ and $$\sqrt{\frac{1}{N}\sum_{i=1}^{N} Z_i^2}$$

are listed in FIG. 11 for 10 particles, each determined from N=120 mobility measurements. The resulting particle sizes ($a=1.03\pm0.03$ μm) correspond well with the range specified by the manufacturer. The accuracy of the particle size measurement in the order of a few nanometers is sufficient to reveal small variations in the sizes of the particles. It is to be noticed that the accuracy of the elementary mobility measurement ($\sigma_{\mu e} \approx 5\times10^{-14}$ m$^2$V$^{-1}$s$^{-1}$) is about 30 times higher than the accuracy of a single mobility measurement ($\sigma \approx 1.3\times10^{-12}$ m$^2$V$^{-1}$s$^{-1}$). The accuracy is higher if the value of $$\sqrt{\frac{1}{N}\sum_{i=1}^{N} Z_i^2}$$

is larger, which can be understood from equation $$\sigma^2_{\mu_e} = \sigma^2 \Big/ \sum_i Z_i^2.$$

The values $\sigma$ and $\sigma_\mu$ are approximately the same, indicating that Brownian motion is the main source of error. Because in this experiment monodisperse particles were used with known average size $a=1.05$ μm, information regarding the size a can be combined with the obtained $\mu_e$ to estimate e the elementary charge, using equation $e=6\pi\eta a\mu_e$. The obtained value for the elementary charge for the 10 particles, i.e. $e=(1.64\pm0.05)\times10^{-19}$ C corresponds with the well known value for e.

In some experiments it has been found that the charge on a silica particle fluctuates with about one exchange (charge±1 e) per second. Such fluctuations can not be observed with conventional methods that average over large numbers of particles and/or longer time intervals. The principle charging mechanism for silica particles charge in water is dissociation of silanol groups, $SiOH \leftrightarrows SiO^- + H^+$. The latter illustrates that such experiments thus may assist in understanding the processes that are occurring.

Figure 9:
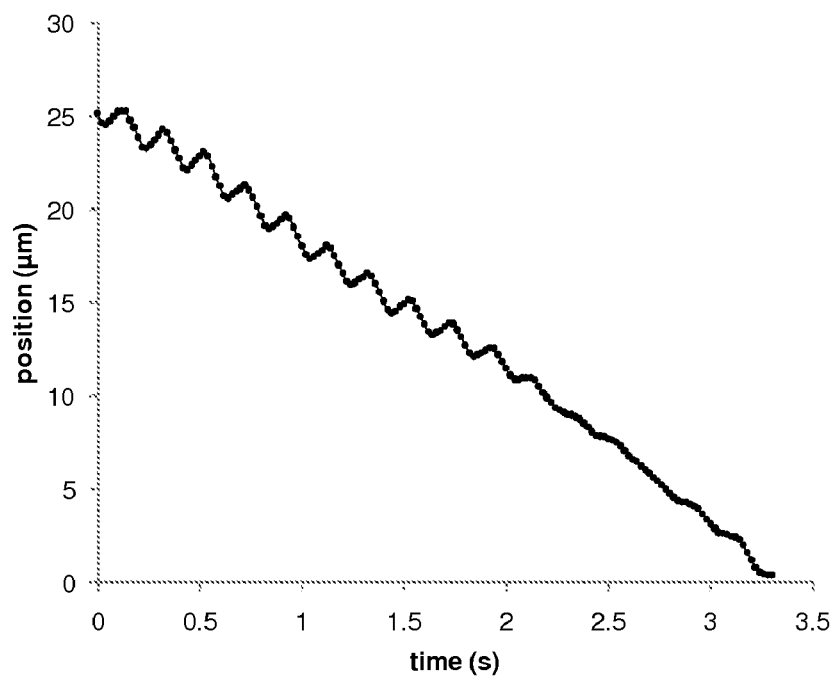
FIG. 9 is an example of an electrophoretic measurement on a polystyrene particle in deionized water with 26% polyethyleneglycol (PEG) and 0.05% acetic acid, indicating the particle position as a function of time, as can be obtained using a method according to an embodiment of the present invention.

In the second example, an electrophoretic cell was used as shown in FIG. 4c. FIG. 9 shows the particle motion in the direction of the electric field of a single particle which was located in the channel of the electrophoretic cell. A square wave voltage was applied with amplitude 112.5V and frequency 5 Hz. Particles (polystyrene) were used with diameter 190 nm in de-ionised water with 26% PEG and 0.05% acetic acid. The particles were fluorescent with excitation wavelength 548 nm, and were visualized using a fluorescence microscope and an EMCCD camera. The particle motion was partly due to a continuous flow in the cell, and partly due to electrophoresis with a square wave voltage. Changes in the amplitude of the particle motion indicated changes of the particle mobility and consequently of the particle charge.

Figure 10:
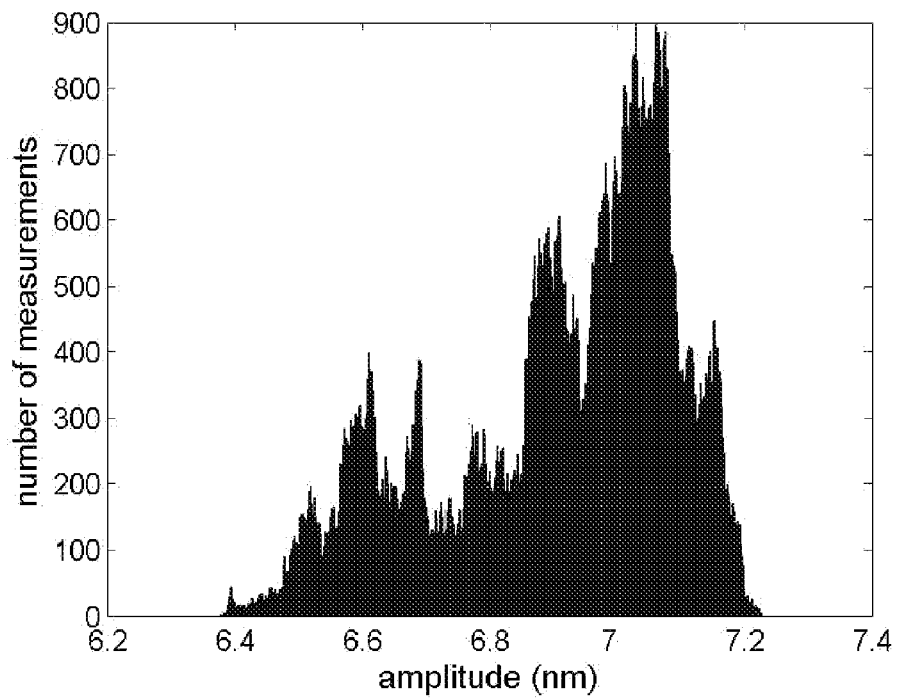
FIG. 10 is an example of a histogram of the amplitude of the oscillation of an optically trapped particle in a sinusoidal field, as can be obtained using a method according to an embodiment of the present invention.

In the third example, an electrophoretic cell was used as shown in FIG. 4c and with an optical trapping setup as shown in FIG. 4d. The strength of the optical trap was previously determined to be 400 pN/μm, which results in a corner frequency of 25 Hz above which the particle motion was not influenced by the trap. A particle (polystyrene) with diameter 500 nm in a solution of de-ionized water containing PEG was optically trapped. The particle position in the direction of the electric field was determined using a quadrant detector with sample frequency 100 kHz for a total measurement time of 300 s. A sinusoidal voltage was applied with amplitude 250V and frequency 500 Hz. The applied voltage signal was also recorded as a function of time. In total $3\times10^7$ samples of the particle position ware obtained. Per period (2 ms) of the sine, the amplitude of the oscillation of the particle (at the fundamental frequency of 500 Hz) was determined by first multiplying the position signal with the applied voltage signal (shifted by the phase difference between the two signals), then taking the average of this product over one period (2 ms) and finally dividing by the amplitude of the applied voltage. Noise at high frequencies was then filtered out by taking a moving average with a window of 0.5 s. FIG. 10 shows a histogram of the resulting 150000 values for the amplitude of the particle oscillation, which is proportional to the mobility of the particle and thus to its charge. The second and third example illustrate how particle properties such as diameter or charge could be determined for particles in polar liquids. The latter may be used to characterize particles or to determine changes of particles, e.g. by binding of a target on a binding site on the particle. These examples thus illustrate advantages and possibilities of embodiments of the methods and/or systems as described above.

It is to be understood that although preferred embodiments, specific constructions and configurations, as well as materials, have been discussed herein for devices according to the present invention, various changes or modifications in form and detail may be made without departing from the scope of this invention as defined by the appended claims. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A method for determining particle properties of particles in a liquid, the method comprising the steps:
   determining an electric mobility distribution, said distribution being a distribution of the electric mobility of individual particles, based on determination of a plurality of values for the electric mobility of an individual particle, the determining being based on detection of individual particles, and
   deriving a particle property based on a periodicity in the electric mobility distribution, the periodicity being characteristic for an electrical characteristic $\mu_e$, said characteristic being the elementary mobility of a particle with charge e.

2. The method according to claim 1, wherein the periodicity is caused by jumps over a value $\mu_e$ being the elementary mobility of a particle corresponding with the difference in mobility when a particle charge reduces or increase with a single elementary charge.

3. The method according to claim 1, wherein the electric mobility is determined in an electrical field having an electric field amplitude of $10^6$V/m or higher.

4. The method according to claim 1, wherein determining a plurality of values for the electric mobility of an individual particle comprises determining a plurality of values for one individual particle over time.

5. The method according to claim 1, wherein determining a plurality of values for the electric mobility of an individual particle comprises determining for a plurality of particles a value of an electric mobility for each particle individually.

6. The method according to claim 1, wherein determining a plurality of values for the electric mobility of an individual particle comprise performing an electrophoretic measurement on at least one individual particle.

7. The method according to claim 1, wherein determining a plurality of values of the electric mobility comprises applying an electric field and detecting the motion of at least one particle as function of the electric field so as to determine the electric mobility.

8. The method according to claim 7, wherein detecting the motion of the particle is performed by optically monitoring the motion of at least one particle.

9. The method according to claim 1, wherein the particle property is any of a charge or a size.

10. The method according to claim 1, comprising:
    deriving a property of the liquid in which the particles are dispensed, based on the determined particle property.

11. The method according to claim 1 for use in a biosensing method for detecting a biological, chemical or bio-chemical event.

12. A system for determining particle properties of particles in a liquid, the system comprising a means adapted for determining an electric mobility distribution, said distribution being a distribution of the electric mobility of individual particles, based on determination of a plurality of values for the electric mobility of an individual particle, the means adapted for determining being based on detection of individual particles and a means adapted for deriving a particle property based on a periodicity in the electric mobility distribution, the periodicity being characteristic for an electrical characteristic $\mu_e$, said characteristic being the elementary mobility of a particle with charge e.

13. The system according to claim 12, wherein the means adapted for determining an electric mobility distribution comprises an electric field generating means and a detection means adapted for detecting movement of at least one particle.

14. The system according to claim 13, wherein the system furthermore comprises a measurement channel for introducing the particles dispensed in a liquid, the portion over which an electric field is placed having characteristic dimensions smaller than 250 μm.

15. The system according to claim 14, the system comprising a biosensor for sensing a biological, chemical or biochemical event.

16. A controller adapted for controlling operation of a system according to a method for determining particle properties, the method comprising:
    determining an electric mobility distribution, said distribution being a distribution of the electric mobility of individual particles, based on determination of a plurality of values for the electric mobility of an individual particle, the determining being based on detection of individual particles, and
    deriving a particle property based on a periodicity in the electric mobility distribution, the periodicity being characteristic for an electrical characteristic $\mu_e$, said characteristic being the elementary mobility of a particle with charge e.

17. The controller according to claim 16, the controller comprising a computer program product adapted to perform the method for determining particle properties, when executed on a computing device.

* * * * *